(12) United States Patent
Takahashi et al.

(10) Patent No.: US 6,677,390 B1
(45) Date of Patent: Jan. 13, 2004

(54) PHOTOCURABLE COMPOSITION CONTAINING IODONIUM SALT COMPOUND

(75) Inventors: Eiji Takahashi, Ichihara (JP); Akihiro Shirai, Ichihara (JP); Hiroshi Takahashi, Chigasaki (JP); Shinichi Kimizuka, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 156 days.

(21) Appl. No.: 10/048,805

(22) PCT Filed: Aug. 1, 2000

(86) PCT No.: PCT/JP00/05090

§ 371 (c)(1),
(2), (4) Date: Jan. 31, 2002

(87) PCT Pub. No.: WO01/09075

PCT Pub. Date: Feb. 8, 2001

(30) Foreign Application Priority Data

Aug. 2, 1999 (JP) ............................. 11-219009

(51) Int. Cl.[7] .............................. C08F 2/50; C08F 4/00; C08G 85/00
(52) U.S. Cl. ............................. 522/31; 522/15; 522/6; 522/25; 522/113; 522/122; 522/121; 522/71; 522/150; 522/168; 522/170; 522/182; 522/154
(58) Field of Search .............................. 522/6, 15, 25, 522/31, 71, 170, 182, 113, 120, 121, 122, 150

(56) References Cited

U.S. PATENT DOCUMENTS

| | | | |
|---|---|---|---|
| 3,862,333 A | | 1/1975 | Chalupda et al. |
| 4,593,052 A | * | 6/1986 | Irving ......................... 522/31 |
| 4,657,779 A | * | 4/1987 | Gaske ........................ 427/512 |
| 4,683,317 A | * | 7/1987 | Crivello et al. ............... 556/64 |
| 4,840,977 A | * | 6/1989 | Crivello et al. ............... 522/25 |
| 4,874,798 A | * | 10/1989 | Koleske et al. .............. 522/31 |
| 4,981,881 A | * | 1/1991 | Crivello et al. .............. 522/31 |
| 5,073,643 A | * | 12/1991 | Crivello ....................... 556/64 |
| 5,079,378 A | * | 1/1992 | Crivello ....................... 556/64 |
| 5,086,086 A | * | 2/1992 | Brown-Wensley et al. ... 522/25 |
| 5,086,192 A | * | 2/1992 | Kessel et al. .................. 556/9 |
| 5,102,771 A | * | 4/1992 | Vogel et al. .............. 430/270.1 |
| 5,141,840 A | * | 8/1992 | Mizutani et al. ......... 430/281.1 |
| 5,144,051 A | * | 9/1992 | Kessel et al. ................. 556/64 |
| 5,318,808 A | * | 6/1994 | Crivello et al. ............. 427/517 |
| 5,384,339 A | * | 1/1995 | Starkey ......................... 522/3 |
| 5,393,641 A | * | 2/1995 | Ito et al. .................. 430/270.1 |
| 5,514,728 A | * | 5/1996 | Lamanna et al. ............. 522/31 |
| 5,703,137 A | * | 12/1997 | Priou et al. ................... 522/25 |
| 5,837,420 A | * | 11/1998 | Aoai et al. ................ 430/270.1 |
| 5,914,219 A | * | 6/1999 | Funhoff et al. ............. 430/326 |
| 6,010,820 A | * | 1/2000 | Aoai et al. ................ 430/270.1 |
| 6,291,540 B1 | * | 9/2001 | Priou et al. ................... 522/31 |
| 6,306,555 B1 | * | 10/2001 | Schulz et al. ............. 430/270.1 |
| 6,365,643 B1 | * | 4/2002 | Oestreich et al. ............. 522/31 |
| 6,380,277 B1 | * | 4/2002 | Oestreich et al. ............. 522/31 |
| 6,440,634 B1 | * | 8/2002 | Ohsawa et al. ........... 430/270.1 |
| 6,537,718 B2 | * | 3/2003 | Nishiyama et al. ......... 430/170 |

FOREIGN PATENT DOCUMENTS

| | | |
|---|---|---|
| JP | 50-151996 A | 12/1975 |
| JP | 60-047029 A | 3/1985 |
| JP | 61-166543 A | 7/1986 |

* cited by examiner

*Primary Examiner*—James J. Seidleck
*Assistant Examiner*—Sanza McClendon
(74) *Attorney, Agent, or Firm*—Dennis G. LaPointe; Mason Law, P.A.

(57) ABSTRACT

An iodonium salt compound which is colored little, can be easily synthesized in high yield, is highly sensitive to irradiation with actinic energy rays such as light, electronic beams, or X-rays, is highly soluble in monomers, and is lowly toxic; and a photocurable composition which can cure in a short time even when the counter anion is a hexafluorophosphonate, tetrafluoroborate, etc., regardless of whether it is clear or pigmented, and which gives a cured object having excellent properties. The photocurable composition is prepared by compounding an iodonium salt compound represented by the general formula (I) with a cationically polymerizable compound, a sensitizer, etc.

37 Claims, No Drawings

PHOTOCURABLE COMPOSITION CONTAINING IODONIUM SALT COMPOUND

TECHNOLOGICAL FIELDS

The present invention relates to novel iodonium salt compounds and photocurable compositions containing the said compounds. In more detail, it relates to cationically photocurable compositions that generate acids and cure in a short time when actinic energy rays, such as light, electron beams and X-rays, are irradiated. The cured products of the said compositions have excellent physical properties so that the compositions are preferably used in paints, adhesives, photoresists, inks, silicon releases and the like.

BACKGROUND ART

Japanese Patents Laid-open Nos. Sho 50-151996, Sho 60-47029 and others describe iodonium salt compounds similar to those of the present invention. They describe also that these iodonium salt compounds can be used as catalysts to cure cationically polymerizable compounds, such as epoxy compounds, with radiation, such as light, electron beams or X-rays.

Generally, iodonium salt compounds have such problems as low solubility in monomers and high toxicity.

It is known that the photocurable properties of iodonium salt compounds are extremely reduced if the counter anions of the compounds are those other than hexafluoroantimonate or tetraperfluorophenylborate, such as hexafluorophosphate or tetrafluoroborate. Therefore, iodonium salt compounds having these counter anions are not suitable to cure clear compositions or compositions containing pigments by light. Sensitizers effective to them have not yet been found either.

DISCLOSURE OF INVENTION

It is an object of the present invention to provide an iodonium salt compound which is colored little, can be easily synthesized in high yield, produces an acid thanks to being highly sensitive to irradiation with actinic energy rays such as light, electronic beams or X-rays, is highly soluble in monomers, and is less toxic. It is also an object to provide a photocurable composition that can cure in a short time even when the counter anion is hexafluorophosphate, tetrafluoroborate or the like, regardless of being clear or pigmented, and that produces a cured object having excellent properties. Particularly it is an object to provide a compound that is much less toxic, such as negative mutagenicity, than known compounds.

In other words, the present invention relates to a compound represented by Formula [I] shown below, and more preferably to an iodonium salt compound represented by Formula [II].

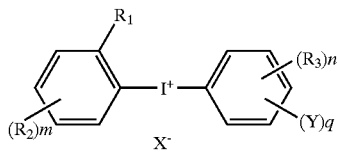
(I)

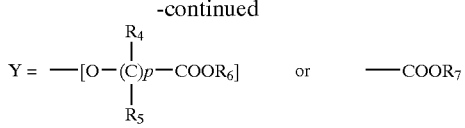

[wherein, $R_1$ is straight-chain or branched alkyl having 1 to 6 carbons;
$R_2$ is straight-chain or branched alkyl having 1 to 6 carbons;
m is an integer of 1 to 4, and $R_2$ groups may be each different when m is 2 or larger;
$R_3$ is straight-chain or branched alkyl having 1 to 6 carbons;
n is 0 or an integer of 1 to 4, and $R_3$ groups may be each different when n is 2 or larger;
Y is represented by the formula shown above, q is an integer of 1 to 5, and Y's may be each different when q is 2 or larger;
$R_4$ and $R_5$ are, each independently, hydrogen, straight-chain or branched alkyl having 1 to 6 carbons, phenyl or aralkyl;
p is an integer of 1 or 2, and $R_4$ and $R_5$ may be each different when p is 2;
$R_6$ and $R_7$ are, each independently, hydrogen, straight-chain or branched alkyl having 1 to 12 carbons, optionally substituted phenyl or optionally substituted aralkyl; and
X is a non-nucleophilic anionic residue.]

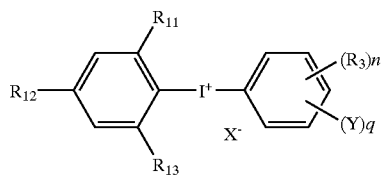
(II)

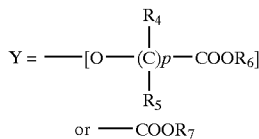

[wherein, $R_{11}$, $R_{12}$ and $R_{13}$ are, each independently, straight-chain or branched alkyl having 1 to 6 carbons;
$R_3$ is straight-chain or branched alkyl having 1 to 6 carbons;
n is 0 or an integer of 1 to 4, and $R_3$ groups may be each different when n is 2 or larger;
Y is represented by the formula shown above, q is an integer of 1 to 5, and Y's may be each different when q is 2 or larger;
$R_4$ and $R_5$ are, each independently, hydrogen, straight-chain or branched alkyl having 1 to 6 carbons, phenyl or aralkyl;
p is an integer of 1 or 2, and $R_4$ and $R_5$ may be each different when p is 2;
$R_6$ and $R_7$ are, each independently, hydrogen, straight-chain or branched alkyl having 1 to 12 carbons, optionally substituted phenyl or optionally substituted aralkyl; and
X is a non-nucleophilic anionic residue.]

This invention also relates to an iodonium salt compound whose non-nucleophilic anionic residue is either $SbF_6$, $AsF_6$, $PF_6$, $BF_4$ or $(F_5C_6)_4B$.

The present invention also relates to a photoacid generator and a photopolymerization initiator both of which contain at least one of the said iodonium salt compounds.

Furthermore, the present invention relates to a photocurable composition containing at least one of the said iodonium salt compounds and cationically polymerizable compounds, a photocurable compositions containing at least one of the said iodonium salt compounds, cationically polymerizable compounds and sensitizers, and a photocurable composition containing further pigments and radically polymerizable compounds in addition to at least one of the said iodonium salt compounds, cationically polymerizable compounds and sensitizers.

Actual examples of the straight-chain or branched alkyl groups having 1 to 6 carbons, of $R_1$, $R_2$, $R_3$, $R_4$, $R_5$, $R_{11}$, $R_{12}$ and $R_{13}$ of the said Formulae [I] and [II] include methyl, ethyl, n-propyl, isopropyl, n-butyl, isobutyl, sec-butyl, t-butyl, n-pentyl, isopentyl, sec-pentyl, t-pentyl, neopentyl, n-hexyl and isohexyl.

Examples of the aralkyl groups of $R_4$ and $R_5$ include benzyl and phenethyl.

$R_6$ and $R_7$ are alkyl groups having up to 12 carbons, such as methyl, ethyl, n-propyl, isopropyl, n-butyl, isobutyl, sec-butyl, t-butyl, n-pentyl, isopentyl, sec-pentyl, t-pentyl, neopentyl, n-hexyl, isohexyl, heptyl or octyl; or optionally substituted phenyl, or optionally substituted aralkyl such as benzyl or phenethyl. Examples of their substituents include halogen such as chlorine, bromine and fluorine, alkyl groups having ether bonds, and hydroxyl.

X is a non-nucleophilic anionic residue, and is preferred to be $SbF_6$, $AsF_6$, $PF_6$, $BF_4$, $(F_5C_6)_4B$ or the like.

Representative examples of the iodonium salt compounds of the present invention are shown in the following. X in the formulae represents a non-nucleophilic anionic residue, such as $SbF_6$, $AsF_6$, $PF_6$, $BF_4$ or $(F_5C_6)_4B$.

Compound (1)

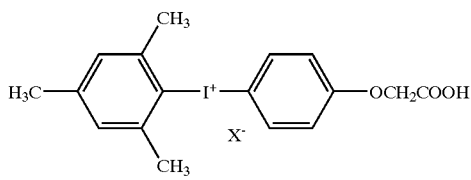

Compound (2)

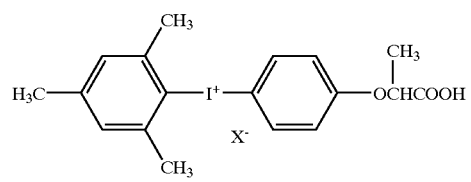

Compound (3)

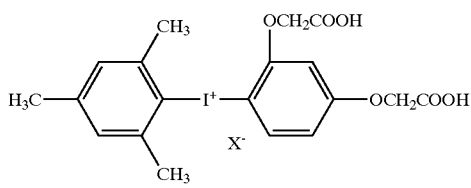

Compound (4)

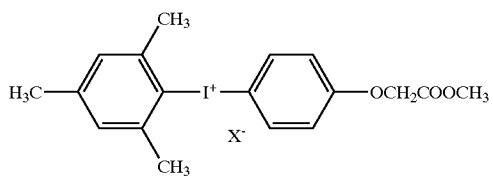

Compound (5)

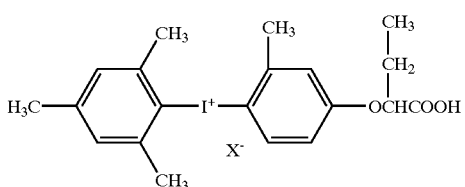

Compound (6)

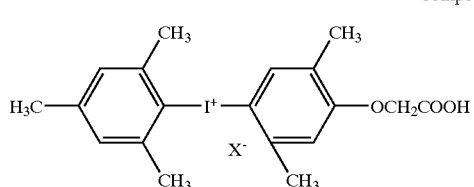

Compound (7)

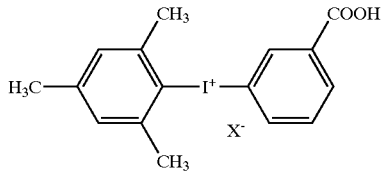

Compound (8)

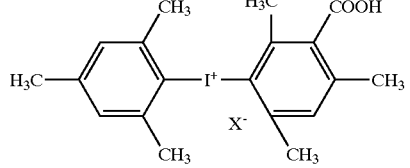

The iodonium salt compounds of Formula [I] of the present invention may be produced according to Reaction Equation A or B [wherein, M is an alkali metal] shown in the following. The reaction of Compounds [a] and [b] with a sulfuric-acid catalyst is carried out, in organic solvents such as acetic acid and acetic anhydride if required, at −20° C. to room temperature for an hour to several 10 hours. After the completion of the reaction, water is added to the reaction solution to stir. Compound [c] is separated by filtration if deposited, or extracted with organic solvents. A salt exchange reaction of Compound [c] obtained gives target Compound [d].

[A]

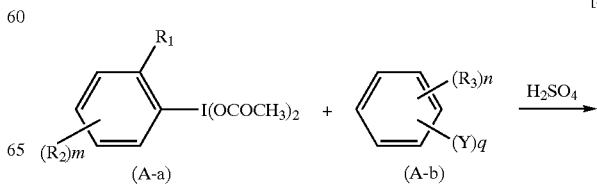

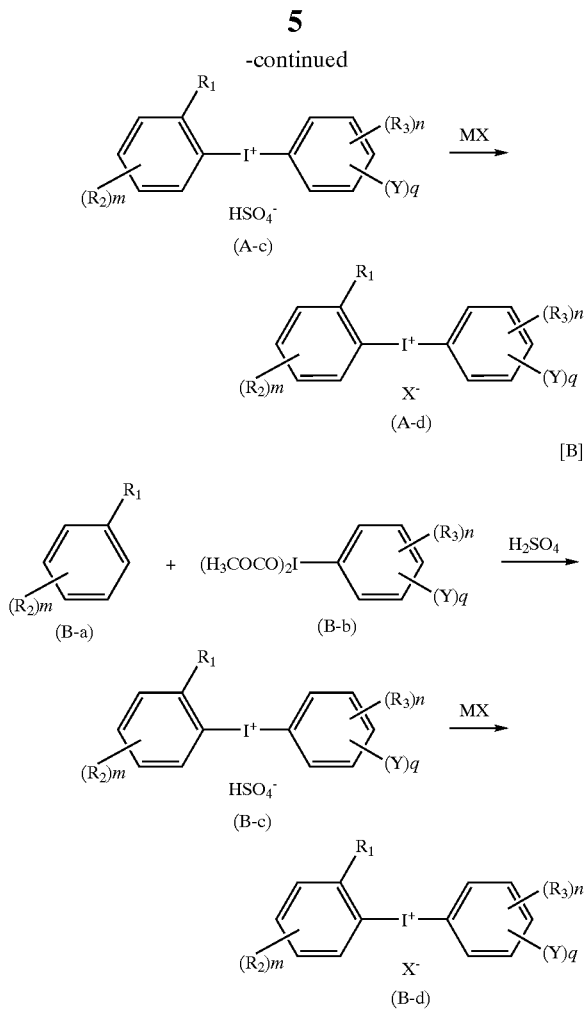

The iodonium salt compounds of the present invention may be used as photoacid generators, and also as photopolymerization initiators to cure cationically polymerizable compounds by irradiation with actinic energy rays such as light, electronic beams or X-rays. Examples of light sources used include low-pressure mercury lamps, medium-pressure mercury lamps, high-pressure mercury lamps, ultra-high-pressure mercury lamps, metal halide lamps, xenon lamps and carbon arc lamps. The compounds may be easily cured by laser light such as semiconductor laser, argon laser or He—Cd laser, or ionizing radiation such as α-rays, β-rays, γ-rays, neutron rays, X-rays or accelerated electron beams. Besides, an iodonium salt compound used together with a sensitizer can cure a cationically polymerizable compound in a shorter time than that without a sensitizer.

Any cationically polymerizable monomers, oligomers and polymers, regardless of their types, can be used as cationically polymerizable compounds in the present invention. Their examples include epoxy compounds of glycidyl ether type, alicyclic epoxy compounds, oxirane compounds such as oxetane compounds, and vinyl ether compounds.

Cationically polymerizable compositions used in the present invention are described in more detail in the following.

(a) Example of vinyl compounds include styrene compounds such as styrene, α-methylstyrene, p-methoxystyrene and p-t-butoxystyrene; alkyl vinyl ether compounds such as methyl vinyl ether, n-butyl vinyl ether, ethyl vinyl ether, isobutyl vinyl ether, cyclohexyl vinyl ether, 2-chloroethyl vinyl ether, 2-phenoxyethyl vinyl ether, 2-hydroxyethyl vinyl ether, 4-hydroxybutyl vinyl ether, stearyl vinyl ether and 2-acetoxyethyl vinyl ether; alkenyl vinyl ether compounds such as allyl vinyl ether, 2-methacryloyloxyethyl vinyl ether and 2-acryloyloxyethyl vinyl ether; aryl vinyl ether compounds such as phenyl vinyl ether and p-methoxyphenyl vinyl ether; cationically polymerizable compounds containing nitrogen such as N-vinylcarbazole and N-vinylpyrolidone; and multifunctional vinyl compounds such as butanediol divinyl ether, triethylene glycol divinyl ether, cyclohexanediol divinyl ether, 1,4-benzenedimethanol divinyl ether, hydroquinone divinyl ether and sazolcinol divinyl ether.

(b) Examples of epoxy compounds include monofunctional monomers such as phenylglycidyl ether, p-tert-butylphenylglycidyl ether, butylglycidyl ether, 2-ethylhexylglycidyl ether, allylglycidyl ether, 1,2-butylene oxide, 1,3-butadiene monoxide, 1,2-dodecylene oxide, epichlorohydrin, 1,2-epoxydecane, ethylene oxide, propylene oxide, styrene oxide, cyclohexene oxide, 3-methacryloyloxymethylcyclohexene oxide, 3-acryloyloxymethylcyclohexene oxide and 3-vinylcyclohexene oxide; and multifunctional epoxy compounds such as 1,13-tetradecadiene dioxide, limonene dioxide, 3,4-epoxycyclohexylmethyl-(3,4-epoxycyclohexyl)carboxylate, di(3,4-epoxycyclohexyl) adipate, bisphenol A-type epoxy resins, bisphenol F-type epoxy resins, o-, m- and p-cresol novolak-type epoxy resins, phenol novolak-type epoxy resins and polyhydric alcohol polyglycidyl ether.

(c) Examples of bicyclo-ortho-ester compounds include 1-phenyl-4-ethyl-2,6,7-trioxabicyclo[2,2,2]octane and 1-ethyl-4-hydroxymethyl-2,6,7-trioxabicyclo[2,2,2]octane.

(d) Examples of spiro-ortho-carbonate compounds include 1,5,7,11-tetraoxaspiro[5,5]undecane, 3,9-dibenzyl-1,5,7,11-tetraoxaspiro[5,5]undecane, 1,4,6-trioxaspiro[4,4]nonane, 2-methyl-1,4,6-trioxaspiro[4,4]nonane and 1,4,6-trioxaspiro[4,5]decane.

(e) Examples of oxetane compounds include 3,3-dimethyloxetane, 3,3-bis(chloromethyl)oxetane, 2-hydroxymethyloxetane, 3-methyl-3-oxetane methanol, 3-methyl-3-methoxymethyloxetane, 3-ethyl-3-phenoxymethyloxetane, resorcinol bis(3-methyl-3-oxetanylethyl) ether and m-xylilene bis(3-ethyl-3-oxetanylethyl ether).

These compounds may be used alone or as a mixture of two or more.

Any compounds that accelerate the photoreactions of the said iodonium salt compounds can be used as sensitizers in the present invention. For example, known sensitizers including coloring matter such as acrydine orange and acrydine yellow and coumarin compounds such as benzoflavin, which are described in Journal of Polymer Science: Polymer Chemistry Edition, Vol. 16, 2441 (1978), and redox compounds with photoradical generators combined, can be used. In addition to these, other examples include phenol derivatives such as 4-methoxyphenol, 4-benzyloxyphenol, 4-methoxy-2-(t-butyl)phenol, hydroquinone, 4-methoxy-1-naphthol and 2-hydroxydibenzofuran; 1-naphthol, 2-naphthol, 1-methoxynaphthalene, 2-methoxynaphthalene, 1-hydroxyphenanthrene, glycidyl-1-naphthyl ether, 2-(2-naphthoxy)ethylvinyl ether, 1,4-dihydroxynaphthalene, 1,5-dihydroxynaphthalene, 1,6-dihydroxynaphthalene, 2,7-dihydroxynaphthalene, 2,7-dimethoxynaphthalene, 1,1'-thiobis(2-naphthol), 1,1'-bi-2-naphthol, 1,5-naphthyldiglycidyl ether, 2,7-di(2-vinyloxyethyl)naphthyl ether, 4-methoxy-1-naphthol, ESN-175 (epoxy resin produced by Shin-nittetu Kagaku Co., Ltd.) or its series of products, epoxy compounds produced by reactions between naphthol derivatives and epichlorohydrin, condensation products of mixtures of naphthol derivatives and phenol derivatives with formalin, epoxy compounds produced by reactions of these condensation products with epichlorohydrin, condensation products of naphthol derivatives and formalin; anthracene derivatives such as 9,10-dimethoxyanthracene, 2-ethyl-9,10-dimethoxyanthracene, 2-t-butyl-9,10-dimethoxyanthracene, 2,3-dimethyl-9,10-dimethoxyanthracene, 9-methoxy-10-methylanthracene, 9,10-diethoxyanthracene, 2-ethyl-9,10-diethoxyanthracene, 2-t-butyl-9,10-diethoxyanthracene, 2,3-dimethyl-9,10-diethoxyanthracene, 9-ethoxy-10-methylanthracene, 9,10-dipropoxyanthracene, 2-ethyl-9,10-dipropoxyanthracene, 2-t-butyl-9,10-dipropoxyanthracene, 2,3-dimethyl-9,10-dipropoxyanthracene, 9-isopropoxy-10-methylanthracene, 9,10-dibenzyloxyanthracene, 2-ethyl-9,10-dibenzyloxyanthracene, 2-t-butyl-9,10-dibenzyloxyanthracene, 2,3-dimethyl-9,10-dibenzyloxyanthracene, 9-benzyloxy-10-methylanthracene, 9,10-di-α-methylbenzyloxyanthracene, 2-ethyl-9,10-di-α-methylbenzyloxyanthracene, 2-t-butyl-9,10-di-α-methylbenzyloxyanthracene, 2,3-dimethyl-9,10-di-α-methylbenzyloxyanthracene and 9-α-methylbenzyloxy)-10-methylanthracene; chrysene derivatives such as 1,4-dimethoxychrysene, 1,4-diethoxychrysene, 1,4-dipropoxychrysene, 1,4-dibenzyloxychrysene and 1,4-di-α-methylbenzyloxychrysene; phenanthrene derivatives such as 9-hydroxyphenanthrene, 9-methoxyphenanthrene, 9-ethoxyphenanthrene, 9-benzyloxyphenanthrene, 9,10-dimethoxyphenanthrene, 9,10-diethoxyphenanthrene, 9,10-dipropoxyphenanthrene, 9,10-dibenzyloxyphenanthrene, 9,10-di-α-methylbenzyloxyphenanthrene, 9-hydroxy-10-methoxyphenanthrene and 9-hydroxy-10-ethoxyphenanthrene; (thio)xanthone derivatives such as xanthone, thioxanthone and 2,4-diethylthioxanthone; and carbazole derivatives such as carbazole, N-vinylcarbazole and N-ethylcarbazole. It is preferable to use, for example, 9,10-dialkoxyanthracene derivatives such as 2-ethyl-9,10-dimethoxyanthracene; phenanthrene derivatives such as 9,10-dimethoxyphenanthrene; thioxanthone derivatives such as 2,4-diethylthioxanthone; carbazole derivatives such as N-ethylcarbazle; and naphthalene derivatives such as 1-naphthol and 2-methoxynaphthalene.

In addition to the above, thioxanthones and a wide variety of dye derivatives can be used that are generally known as sensitizers for iodonium salt compounds.

A compounding ratio of an iodonium salt compound of Formula [I] or [II] with acationically polymerizable compound may be 0.01 to 20 parts (by weight, hereinafter the same), preferably 0.1 to 10 parts, of the former to 100 parts of the latter. If the iodonium salt compound is used in a smaller amount, the cationically polymerizable compound becomes less curable. An excessive amount results in reduced properties of the cured product.

A compounding ratio of an aforementioned sensitizer to a cationically polymerizable compound may be 0.001 to 10 parts, preferably 0.01 to 5 parts, of the former to 100 parts of the latter. If the sensitizer is used in a smaller amount, The photoreactivity of an iodonium salt compound used as a photopolymerization initiator is reduced. An excessive amount results in lowered properties of the cured product. However, sensitizers having cationically polymerizable groups, such as epoxy and vinyl ether groups, can be compounded at arbitrary ratios.

Photocurable compositions of the present invention, if contain pigments, have applications for inks and photoresists. Examples of pigments used in the present invention include black pigments such as carbon black, acetylene black, lamp black and aniline black; yellow pigments such as chrome yellow, zinc yellow, cadmium yellow, yellow iron oxide, mineral fast yellow, nickel titanium yellow, nables yellow, naphthol yellow S, hanza yellow G, hanza yellow 10G, benzizin yellow G, benzizin yellow GR, quinoline yellow lake, permanent yellow NCG and turtrazin lake; orange pigments such as red chrome yellow, molybdenum orange, permanent orange GTR, pyrazolone orange, balcan orange, indanthrene brilliant orange RK, benzizin orange G and indanthrene brilliant orange GK; red pigments such as iron oxide red, cadmium red, minium, cadmium mercury sulfate, permanent red 4R, lisol red, pyrazolone red, watching red calcium salt, lake red D, brilliant carmine 6B, eosine lake, rhodamine lake B, alizarin lake and brilliant carmine 3B; violet pigments such as manganese violet, fast violet B and methyl violet lake; blue pigments such as Berlin blue, cobalt blue, alkali blue lake, Victoria blue lake, phthalocyanine blue, non-metallic phthalocyanine blue, phthalocyanine blue partially chlorinated product, fast sky blue and indanthrene blue BC; green pigments such as chrome green, chromium oxide, pigment green B, malachite green lake and final yellow green G; white pigments such as zinc white, titanium dioxide, antimony white and zinc sulfate; and fillers such as baryta powder, barium carbonate, clay, silica, white carbon, talc and alumina white.

To control physical properties, curability and other properties of the cured products of photocurable compositions in the present invention, radically polymerizable compounds can be used. Any radically polymerizable monomers, oligomers and polymers, regardless of their types, can be used as radically polymerizable compounds in the present invention. Unsaturated ester compounds are particularly preferred. Examples of radically polymerizable monomers include monofunctional and multifunctional acrylate and methacrylate monomers; radically polymerizable oligomers include epoxy acrylate, epoxy methacrylate, polyester acrylate, polyester methacrylate, polyether acrylate, polyether methacrylate, polyurethane acrylate, polyurethane methacrylate, polybutadiene acrylate and polybutadiene methacrylate; and radically polymerizable polymers include acrylates, methacrylates and unsaturated polyesters, such as polyesters, polybutadienes, polyethers, urethanes and epoxy compounds.

Examples of radically polymerizable, reactive diluents include acrylic acid and acrylate monomers such as ethyl acrylate, methacrylic acid and methacrylate monomers such as methyl methacrylate, and styrene.

BEST FORM TO IMPLEMENT THE INVENTION

The present invention is described in more detail in reference to Examples, but is not limited to these examples.

EXAMPLE 1

Synthesis of 4-Carboxymethoxyphenyl-2',4',6'-trimethylphenyliodonium Hexafluorophosphate 5.8 g of phenoxyacetic acid, 13.8 g of iodomesitylene diacetate, 190 g of acetic acid and 17.6 g of acetic anhydride were stirred at room temperature. After iodomesitylene diacetate was dissolved, 3.7 g of sulfuric acid was dropped at 15° C. The resulting solution was stirred at room temperature for 3 hours, and left to stand overnight. An aqueous solution of 7.0 g of potassium hexafluorophosphate dissolved in 50 g of pure water was dropped into the solution with stirring, while cooling with ice. The crude reaction solution was poured into 1L of water. The deposited product was separated by filtration, washed with water, and dried at 40° C. under reduced pressure to give 15.0 g of white powder. It was identified with NMR.

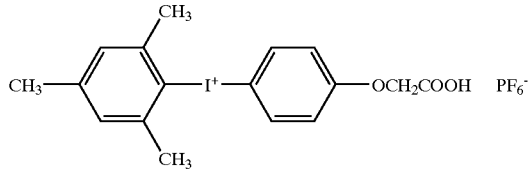

$^1$H NMR ((CD$_3$)$_2$SO); δ=8 2.29, 2.61 (9H, 2s, CH$_3$), 4.76 (2H, s, CH$_2$), 7.02, 7.92 (4H, 2d, IC$_6$H$_4$O), 7.20 (2H, s, (CH$_3$)$_3$C$_6$H$_2$I).

EXAMPLE 2

Synthesis of 4-Methoxycarbonylmethoxyphenyl-2′,4′,6′-trimethylphenyliodonium Hexafluorophosphate Example 1 was repeated except that 6.3 g of methyl phenoxyacetate was used instead of phenoxyacetic acid, to give 19.0 g of white powder. It was identified with NMR.

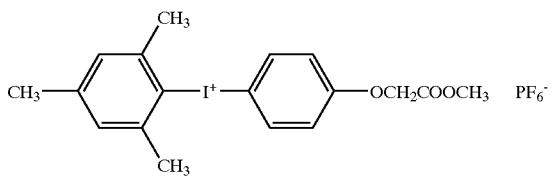

$^1$H NMR ((CD$_3$)$_2$SO); δ=2.29, 2.60 (9H, 2s, CH$_3$), 3.68 (3H, s, CH$_3$OCO), 4.89 (2H, s, CH$_2$), 7.04, 7.92 (4H, 2d. IC$_6$H$_4$O), 7.20 (2H, s, (CH$_3$)$_3$C$_6$H$_2$I).

EXAMPLE 3

Synthesis of 4-Carboxymethylmethoxyphenyl-2′,4′,6′-trimethylphenyliodonium Hexafluorophosphate 6.3 g of 2-phenoxypropionic acid, 13.8 g of iodomesitylene diacetate, 190 g of acetic acid and 17.6 g of acetic anhydride were stirred at room temperature. After iodomesitylene diacetate was dissolved, 3.7 g of sulfuric acid was dropped at 15° C. The resulting solution was stirred at room temperature for 3 hours, and left to stand overnight. An aqueous solution of 7.0 g of potassium hexafluorophosphate dissolved in 50 g of pure water was dropped into the solution with stirring, while cooling with ice. The crude reaction solution was poured into 1L of water, extracted with ethyl acetate, washed with water, and dried at 40° C. under reduced pressure to give 5.1 g of white powder. It was identified with NMR.

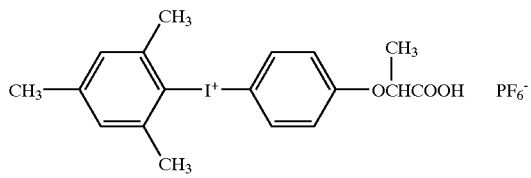

$^1$H NMR ((CD$_3$)$_2$SO); δ=1.49 (3H, d, CH$_3$CH), 2.29, 2.60 (9H, 2s, (CH$_3$)$_3$C$_6$H$_2$I), 4.96 (H, m, CH$_3$CH, 6.96, 7.91 (4H, 2d, IC$_6$H$_4$O), 7.20 (2H, s, (CH$_3$)$_3$C$_6$H$_2$I).

EXAMPLE 4

Synthesis of 3-Carboxyphenyl-2′,4′,6′-trimethylphenyliodonium Hexafluorophosphate 4.6 g of mesitylene, 13.9 g of m-iodobenzoic acid diacetate, 190 g of acetic acid and 17.6 g of acetic anhydride were stirred at room temperature. Then, 3.7 g of sulfuric acid was dropped at 15° C. The resulting solution was stirred at room temperature for 3 hours, and left to stand overnight. An aqueous solution of 7.0 g of potassium hexafluorophosphate dissolved in 50 g of pure water was dropped into the solution with stirring, while cooling with ice. The crude reaction solution was poured into 1L of water. The deposited product was separated by filtration, washed with water, and dried at 40° C. under reduced pressure to give 5.5 g of white powder. It was identified with NMR.

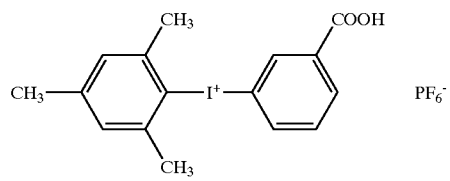

$^1$H NMR ((CD$_3$)$_2$SO); δ=2.301 259 (9H, 2s, (CH$_3$)$_3$C$_6$H$_2$I), 7.22 (2H, s, (CH$_3$)$_3$C$_6$H$_2$I), 7.53, 7.98, 8.05, 8.38 (4H, t, 2d, s, C$_6$H$_4$COOH).

EXAMPLE 5

Synthesis of 4-Isopropoxycarbonylmethoxyphenyl-2′,4′,6′-trimethylphenyliodonium Hexafluorophosphate 2.9 g of isopropyl phenoxyacetate, 5.0 g of iodomesitylene diacetate, 45.0 g of acetic acid and 10.0 g of acetic anhydride were stirred at room temperature. After iodomesitylene diacetate was dissolved, 1.4 g of sulfuric acid was dropped at 15° C. The resulting solution was stirred at room temperature for 3 hours, and left to stand overnight. An aqueous solution of 2.9 g of potassium hexafluorophosphate dissolved in 200 g of pure water was dropped into the solution with stirring, while cooling with ice. The crude reaction solution was poured into 500 ml of water. The deposited product was separated by filtration, washed with water, and dried at 40° C. under reduced pressure to give 5.9 g of white powder. It was identified with NMR.

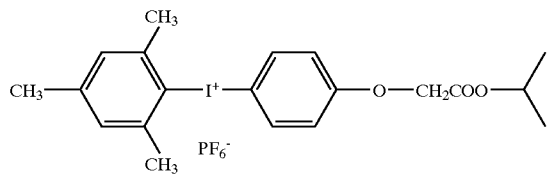

$^1$H NMR ((CD$_3$)$_2$SO); δ=1.18 (6H, s, CH$_3$CH),+2.29, 2.60 (9H, 2s, CH$_3$), 4.83 (2H, s, CH$_2$), 4.96 (1H, m, CH) 7.02, 7.92 (4H, 2d, IC$_6$H$_4$O), 7.20 (2H, s, (CH$_3$)$_3$C$_6$H$_2$I).

EXAMPLE 6

Synthesis of 4-[2-(2-Methoxyethoxy)ethoxy]carbonylmethoxyphenyl-2′,4′,6′-trimethylphenyliodonium Hexafluorophosphate 3.1 g of phenoxyacetic acid diethylene glycol monomethyl ether, 4.0 g of iodomesitylene diacetate, 36.0 g of acetic acid and 9.0 g of acetic anhydride were stirred at room temperature. After iodomesitylene diacetate was dissolved, 1.2 g of sulfuric acid was dropped at 15° C. The resulting solution was stirred at room temperature for 3 hours, and left to stand overnight. An aqueous solution of 2.2 g of potassium hexafluorophosphate dissolved in 200 g of pure water was dropped into the solution with stirring, while cooling with ice. The crude reaction solution was poured into 500 ml of water, extracted with ethyl acetate, washed with water, and dried at 40° C. under reduced pressure to give 4.0 g of yellowish brown oil. It was identified with NMR.

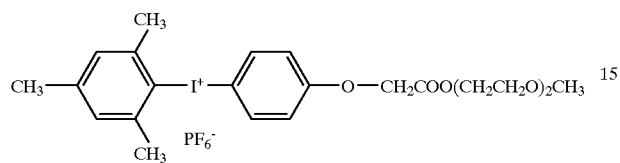

$^1$H NMR ((CD$_3$)$_2$SO); δ=2.29, 2.61 (9H, 2s, CH$_3$), 3.23 (3H, s, CH$_3$O), 3.42, 3.49, 3.60, 4.22 (8H, 3m, t, CH$_2$), 4.90 (2H, s, CH$_2$CO) 7.04, 7.91 (4H, 2d, IC$_6$H$_4$O), 7.20 (2H, s, (CH$_3$)$_3$C$_6$H$_2$I).

EXAMPLE 7

Synthesis of 4-(1-Ethoxycarbonylethoxy)phenyl-2', 4',6'-trimethylphenyliodonium Hexafluorophosphate 2.5 g of ethyl 2-phenoxypropionate, 4.0 g of iodomesitylene diacetate, 36.0 g of acetic acid and 9.0 g of acetic anhydride were stirred at room temperature. After iodomesitylene diacetate was dissolved, 1.2 g of sulfuric acid was dropped at 15° C. The resulting solution was stirred at room temperature for 3 hours, and left to stand overnight. An aqueous solution of 2.2 g of potassium hexafluorophosphate dissolved in 200 g of pure water was dropped into the solution with stirring, while cooling with ice. The crude reaction solution was poured into 500 ml of water. The deposited product was separated by filtration, washed with water, and dried at 40° C. under reduced pressure to give 5.7 g of white powder. It was identified with NMR.

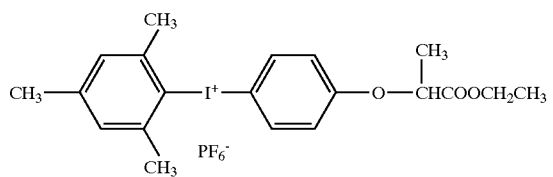

$^1$H NMR ((CD$_3$)$_2$SO); δ=1.14 (3H, t, CH$_3$CH$_2$) 1.50 (3H, d, CH$_3$CH); 2.29, 2.61 (9H, 2s, CH$_3$), 4.12 (2H, m, CH$_2$CH$_3$), 5.08 (1H, m, CH) 6.98, 7.91 (4H, 2d, IC$_6$H$_4$O), 7.20 (2H, s, (CH$_3$)$_3$C$_6$H$_2$I).

EXAMPLE 8

Synthesis of 4-Cyclohexyloxycarbonylmethoxyphenyl-2',4',6'-trimethylphenyliodonium Hexafluorophosphate 2.9 g of cyclohexyl phenoxyacetate, 4.0 g of iodomesitylene diacetate, 36.0 g of acetic acid and 9.0 g of acetic anhydride were stirred at room temperature. After iodomesitylene diacetate was dissolved, 1.2 g of sulfuric acid was dropped at 15° C. The resulting solution was stirred at room temperature for 3 hours, and left to stand overnight. An aqueous solution of 2.1 g of potassium hexafluorophosphate dissolved in 200 g of pure water was dropped into the solution with stirring, while cooling with ice. The crude reaction solution was poured into 500ml of water, extracted with ethyl acetate, washed with water, and dried at 40° C. under reduced pressure to give 3.7 g of reddish brown oil. It was identified with NMR.

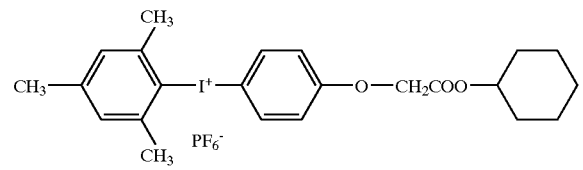

$^1$H NMR ((CD$_3$)$_2$SO); δ=1.11–1.77 (10H, m, CH$_2$), 2.29, 2.60 (9H, 2s, CH$_3$), 4.73 (1H, m, CH), 4.86 (2H, s, CH$_2$CO) 7.03, 7.92 (4H, 2d, IC$_6$H$_4$O), 7.19 (2H, s, (CH$_3$)$_3$C$_6$H$_2$I).

EXAMPLE 9

Synthesis of 4-Carboxymethoxyphenyl-2',5'-dimethylphenyliodonium Hexafluorophosphate 2.6 g of phenoxyacetic acid, 6.0 g of iodo-p-xylene diacetate, 45.0 g of acetic acid and 10.0 g of acetic anhydride were stirred at room temperature. After iodo-p-xylene diacetate was dissolved, 1.8 g of sulfuric acid was dropped at 15° C. The resulting solution was stirred at room temperature for 3 hours, and left to stand overnight. An aqueous solution of 3.2 g of potassium hexafluorophosphate dissolved in 300 g of pure water was dropped into the solution with stirring, while cooling with ice. The crude reaction solution was poured into 1 L of water. The deposited product was separated by filtration, washed with water, and dried at 40° C. under reduced pressure to give 5.6 g of white powder. It was identified with NMR.

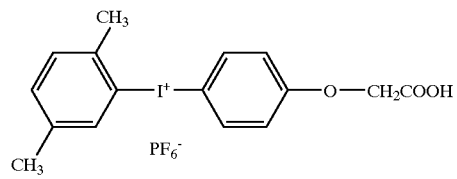

$^1$H NMR ((CD$_3$)$_2$SO); δ=2.30, 2.56 (6H, 2s, CH$_3$), 4.77 (2H, s, CH$_2$), 7.04, 8.11 (4H, 2d, IC$_6$H$_4$O), 7.40, 8.22 (3H, m, s, (CH$_3$)$_2$C$_6$H$_3$I).

EXAMPLE 10

Synthesis of 4-Carboxymethoxyphenyl-2',3',5',6'-tetramethylphenyliodonium Hexafluorophosphate 2.4 g of phenoxyacetic acid, 6.0 g of iododurene diacetate, 45.0 g of acetic acid and 10.0 g of acetic anhydride were stirred at room temperature. After iododurene diacetate was dissolved, 1.7 g of sulfuric acid was dropped at 15° C. The resulting solution was stirred at room temperature for 3 hours, and left to stand overnight. An aqueous solution of 2.9 g of potassium hexafluorophosphate dissolved in 250 g of pure water was dropped into the solution with stirring, while cooling with ice. The crude reaction solution was poured into 1 L of water. The deposited product was separated by filtration, washed with water, and dried at 40° C. under reduced pressure to give 6.0 g of white powder. It was identified with NMR.

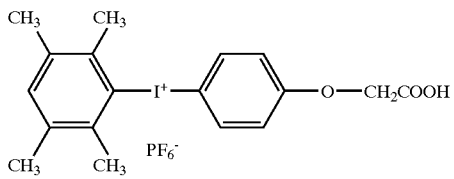

$^1$H NMR ((CD$_3$)$_2$SO); δ=2.31, 2.59 (12H, 2s, CH$_3$), 4.75 (2H, s, CH$_2$), 7.01, 7.90 (4H, 2d, IC$_6$H$_4$O), 7.26 (1H, s, (CH$_3$)$_4$C$_6$HI).

EXAMPLE 11

A part of an iodonium salt compound was compounded with UVR-6110 (alicyclic epoxy compound produced by UCC Co., Ltd.) and, if necessary, a sensitizer. The resulting product was irradiated with a belt-conveyer-type high-pressure mercury lamp (80W). The maximum curing rate was measured. The results are shown in Table 1.

EXAMPLE 12

100 parts of UVR-6110 (alicyclic epoxy compound produced by UCC Co., Ltd.), 100 parts of titanium oxide, 2 parts of an iodonium salt compound and a part of a sensitizer were mixed and kneaded by 3 rollers. The resulting product was irradiated with a belt-conveyer-type gallium doped metal halide lamp (160W). The maximum curing rate was measured. The results are shown in Table 1.

TABLE 1

| | Clear (Example 11) | | | Pigmented (Example 12) | |
|---|---|---|---|---|---|
| | | Type and amount | | | |
| Iodonium salt | No sensitizer | of sensitizer used | Curing rate | Sensitizer (4) | Sensitizer (5) |
| Compound of Example 1 | Cured at 5 m/min | (1): 0.5 part | Cured at 40 m/min | Cured at 20 m/min | Cured at 40 m/min |
| Compound of Example 1 | Cured at 5 m/min | (1): 1.0 part | Cured at over 100 m/min | Cured at 20 m/min | Cured at 40/min |
| Compound of Example 1 | Cured at 5 m/min | (1): 1.0 part | Cured at 100 m/min | Cured at 20 m/min | Cured at 40 m/min |
| Compound of Example 1 | Cured at 5 m/min | (3): 1.0 part | Cured at 100 m/min | Cured at 20 m/min | Cured at 40 m/min |
| Compound of Example 2 | Cured at 5 m/min | (1): 0.5 part | Cured at over 40 m/min | Cured at 20 m/min | Cured at 40 m/min |
| Compound of Example 3 | Cured at 5 m/min | (1): 0.5 part | Cured at over 40 m/min | Cured at 20 m/min | Cured at 40 m/min |
| Compound of Example 4 | Cured at 5 m/min | (1): 0.5 part | Cured at over 40 m/min | Cured at 20 m/min | Cured at 40 m/min |
| Compound of Example 5 | Cured at 5 m/min | (1): 0.5 part | Cured at 40 m/min | Cured at 20 m/min | Cured at 40 m/min |
| Compound of Example 5 | Cured at 5 m/min | (1): 1.0 part | Cured at over 100 m/min | Cured at 20 m/min | Cured at 40 m/min |
| Compound of Example 6 | Cured at 5 m/min | (1): 0.5 part | Cured at 40 m/min | Cured at 20 m/min | Cured at 40 m/min |
| Compound of Example 7 | Cured at 5 m/min | (1): 0.5 part | Cured at 40 m/min | Cured at 20 m/min | Cured at 40 m/min |
| Compound of Example 7 | Cured at 5 m/min | (1): 1.0 part | Cured at over 100 m/min | Cured at 20 m/min | Cured at 40 m/min |
| Compound of Example 7 | Cured at 5 m/min | (2): 1.0 part | Cured at over 100 m/min | Cured at 20 m/min | Cured at 40 m/min |
| Compound of Example 7 | Cured at 5 m/min | (3): 1.0 part | Cured at over 100 m/min | Cured at 20 m/min | Cured at 40 m/min |
| Compound of Example 8 | Cured at 5 m/min | (1): 0.5 part | Cured at 40 m/min | Cured at 20 m/min | Cured at 40 m/min |
| Compound of Example 8 | Cured at 5 m/min | (1): 1.0 part | Cured at over 100 m/min | Cured at 20 m/min | Cured at 40 m/min |
| Compound of Example 9 | Cured at 5 m/min | (1): 0.5 part | Cured at 40 m/min | Cured at 20 m/min | Cured at 40 m/min |
| Compound of Example 9 | Cured at 5 m/min | (1): 1.0 part | Cured at over 100 m/min | Cured at 20 m/min | Cured at 40 m/min |
| Compound of Example 10 | Cured at 5 m/min | (1): 0.5 part | Cured at 40 m/min | Cured at 20 m/min | Cured at 40 m/min |
| Compound of Example 10 | Cured at 5 m/min | (1): 1.0 part | Cured at over 100 m/min | Cured at 20 m/min | Cured at 40 m/min |

Sensitizers:
(1) 1-Naphthol
(2) 9,10-Dimethoxyphenanthrene
(3) N-ethylcarbazole
(4) 2,4-Dimethylthioxanthone
(5) 2-Ethyl-9,10-dimethoxyanthracene As seen from Table 1, the photocurable compositions of the present invention, particularly those produced with iodonium salt compounds and sensitizers, cured by UV irradiation in a short time. It was thus found that photocurable compositions with excellent physical properties could be obtained.

The compounds described in Examples above are negative in mutagenicity tests. The photocurable compositions of the present invention have been confirmed to be less toxic.

Industrial Availability

The iodonium salt compounds of the present invention are colorless solids, can be synthesized easily in high yields, and are much less toxic than known compounds. They also act as excellent photoacid generators. Particularly when used together with sensitizers, the compounds are very photoreactive, regardless of being clear or pigmented, and cure cationically polymerizable compounds in a short time by irradiation with actinic energy rays such as light, electron beams or X-rays. In addition, cured products of the said compositions have excellent physical properties so that the compositions can be favorably used in paints, adhesives, photoresists, inks, silicon releases and the like.

What is claimed:

1. An iodonium salt compound represented by Formula [I]

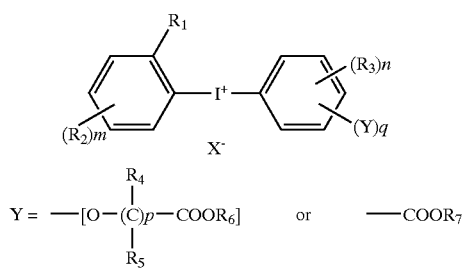

[wherein, $R_1$ is straight-chain or branched alkyl having 1 to 6 carbons;

$R_2$ is straight-chain or branched alkyl having 1 to 6 carbons;

m is an integer of 1 to 4, and $R_2$ groups may be each different when m is 2 or larger;

$R_3$ is straight-chain or branched alkyl having 1 to 6 carbons;

n is 0 or an integer of 1 to 4, and $R_3$ groups may be each different when n is 2 or larger;

Y is represented by the formula shown above, q is an integer of 1 to 5, and Y's may be each different when q is 2 or larger;

$R_4$ and $R_5$ are, each independently, hydrogen, straight-chain or branched alkyl having 1 to 6 carbons, phenyl or aralkyl;

p is an integer of 1 or 2, and $R_4$ and $R_5$ may be each different when p is 2;

$R_6$ and $R_7$ are, each independently, hydrogen, optionally, substituted straight-chain or branched alkyl having 1 to 12 carbons, optionally substituted phenyl or optionally substituted aralkyl; and X is a non-nucleophilic anionic residue.]

2. An iodonium salt compound represented by Formula [II] according to claim 1

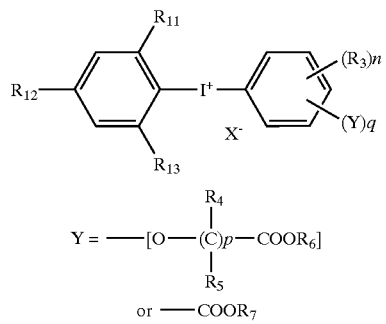

[wherein, $R_{11}$, $R_{12}$ and $R_{13}$ are, each independently, straight-chain or branched alkyl having 1 to 6 carbons;

$R_3$ is straight-chain or branched alkyl having 1 to 6 carbons;

n is 0 or an integer of 1 to 4, and $R_3$ groups may be each different when n is 2 or larger;

Y is represented by the formula shown above, q is an integer of 1 to 5, and Y's may be each different when q is 2 or larger;

$R_4$ and $R_5$ are, each independently, hydrogen, straight-chain or branched alkyl having 1 to 6 carbons, phenyl or aralkyl;

p is an integer of 1 or 2, and $R_4$ and $R_5$ may be each different when p is 2;

$R_6$ and $R_7$ are, each independently, hydrogen, straight-chain or branched alkyl having 1 to 12 carbons, optionally substituted phenyl or optionally substituted aralkyl; and X is a non-nucleophilic anionic residue.]

3. An iodonium salt compound according to claim 1, in which the non-nucleophilic anionic residue is one of $SbF_6$, $AsF_6$, $PF_6$, $BF_4$ or $(F_5C_6)_4B$.

4. An iodonium salt compound according to claim 2, in which the non-nucleophilic anionic residue is one of $SbF_6$, $AsF_6$, $PF_6$, $BF_4$ or $(F_5C_6)_4B$.

5. A photoacid generator containing at least one of the iodonium salt compounds according to claim 1.

6. A photoacid generator containing at least one of the iodonium salt compounds according to claim 2.

7. A photoacid generator containing at least one of the iodonium salt compounds according to claim 3.

8. A photoacid generator containing at least one of the iodonium salt compounds according to claim 4.

9. A photopolymerization initiator containing at least one of the iodonium salt compounds according to claim 1.

10. A photopolymerization initiator containing at least one of the iodonium salt compounds according to claim 2.

11. A photopolymerization initiator containing at least one of the iodonium salt compounds according to claim 3.

12. A photopolymerization initiator containing at least one of the iodonium salt compounds according to claim 4.

13. A photocurable composition containing at least one of the iodonium salt compounds according to claim 1, and a cationically polymerizable compound.

14. A photocurable composition containing at least one of the iodonium salt compounds according to claim 2, and a cationically polymerizable compound.

15. A photocurable composition containing at least one of the iodonium salt compounds according to claim 3, and a cationically polymerizable compound.

16. A photocurable composition containing at least one of the iodonium salt compounds according to claim 4, and a cationically polymerizable compound.

17. A photocurable composition according to claim 13, in which the composition further contains a sensitizer.

18. A photocurable composition according to claim 14, in which the composition further contains a sensitizer.

19. A photocurable composition according to claim 15, in which the composition further contains a sensitizer.

20. A photocurable composition according to claim 16, in which the composition further contains a sensitizer.

21. A photocurable composition according to claim 17, in which the sensitizer is one or two or more compounds selected from the group consisting of 9,10-dialkoxyanthracene derivatives, phenanthrene derivatives, thioxanthone derivatives, carbazole derivatives and naphthalene derivatives.

22. A photocurable composition according to claim 18, in which the sensitizer is one or two or more compounds selected from the group consisting of 9,10-dialkoxyanthracene derivatives, phenanthrene derivatives, thioxanthone derivatives, carbazole derivatives and naphthalene derivatives.

23. A photocurable composition according to claim 19, in which the sensitizer is one or two or more compounds selected from the group consisting of 9,10-dialkoxyanthracene derivatives, phenanthrene derivatives, thioxanthone derivatives, carbazole derivatives and naphthalene derivatives.

24. A photocurable composition according to claim 20, in which the sensitizer is one or two or more compounds selected from the group consisting of 9,10-dialkoxyanthracene derivatives, phenanthrene derivatives, thioxanthone derivatives, carbazole derivatives and naphthalene derivatives.

25. A photocurable composition according to claim 13, in which the composition further contains pigments.

26. A photocurable composition according to claim 14, in which the composition further contains pigments.

27. A photocurable composition according to claim 15, in which the composition further contains pigments.

28. A photocurable composition according to claim 16, in which the composition further contains pigments.

29. A photocurable composition according to claim 17, in which the composition further contains pigments.

30. A photocurable composition according to claim 18, in which the composition further contains pigments.

31. A photocurable composition according to claim 19, in which the composition further contains pigments.

32. A photocurable composition according to claim 20, in which the composition further contains pigments.

33. A photocurable composition according to claim 21, in which the composition further contains pigments.

34. A photocurable composition according to claim 22, in which the composition further contains pigments.

35. A photocurable composition according to claim 23, in which the composition further contains pigments.

36. A photocurable composition according to claim 24, in which the composition further contains pigments.

37. A photocurable composition according to any one of claim 13 to 36 in which the composition further contains radically polymerizable compounds.

* * * * *

UNITED STATES PATENT AND TRADEMARK OFFICE
CERTIFICATE OF CORRECTION

PATENT NO. : 6,677,390 B1  Page 1 of 1
APPLICATION NO. : 10/048805
DATED : January 13, 2004
INVENTOR(S) : Takahashi et al.

It is certified that error appears in the above-identified patent and that said Letters Patent is hereby corrected as shown below:

On title page, item (75) Inventors
replace Inventors's cities are follows:

Eiji Takahashi, "Chiba"
Akihiro Shirai, "Chiba"
Hiroshi Takahashi, "Kanagawa"
Shinichi Kimizuka, Chiba Col. 9, line 15
delete "8"

Col. 10, line 32
delete "I"
and replace with --"i"--.

Signed and Sealed this

First Day of January, 2008

JON W. DUDAS
*Director of the United States Patent and Trademark Office*